United States Patent [19]

Peters

[11] 4,062,605
[45] Dec. 13, 1977

[54] PORTABLE SEATING APPARATUS
[75] Inventor: Peter A. C. Peters, San Diego, Calif.
[73] Assignee: The United States of America as represented by the Secretary of the Navy, Washingtn, D.C.
[21] Appl. No.: 729,049
[22] Filed: Oct. 4, 1976
[51] Int. Cl.$^2$ ............................................ A47B 83/00
[52] U.S. Cl. ................................ 312/235 R; 297/437
[58] Field of Search .................. 312/235; 297/423, 432, 297/437

[56] References Cited
U.S. PATENT DOCUMENTS

| | | | |
|---|---|---|---|
| 1,301,248 | 4/1919 | Fuller | 297/437 X |
| 1,501,637 | 7/1924 | Wallin | 312/235 R |
| 1,564,339 | 12/1925 | Fraser et al. | 297/437 X |
| 2,495,374 | 1/1950 | Horn | 312/235 R |
| 2,547,754 | 4/1951 | Herrick | 312/235 R |
| 2,628,879 | 2/1953 | Schultz | 297/432 X |
| 2,678,461 | 5/1954 | Johnson | 312/235 R |
| 3,000,683 | 9/1961 | MacNeary | 312/235 R |

Primary Examiner—Paul R. Gilliam
Assistant Examiner—Victor N. Sakran
Attorney, Agent, or Firm—R. S. Sciascia; G. J. Rubens

[57] ABSTRACT

A portable seating bench for positioning subjects for anthropometric measurements provides a flat surface upon which a subject may be seated, the flat surface comprising a part of a containing means. Supporting structure is provided to support the flat surface and a subject seated thereon and to support or otherwise position the feet of the subject while a set of anthropometric measurements are made with portable measuring devices, all such support structure and measuring devices being of such dimensions that they may be contained within the containing means for transport or storage.

9 Claims, 4 Drawing Figures

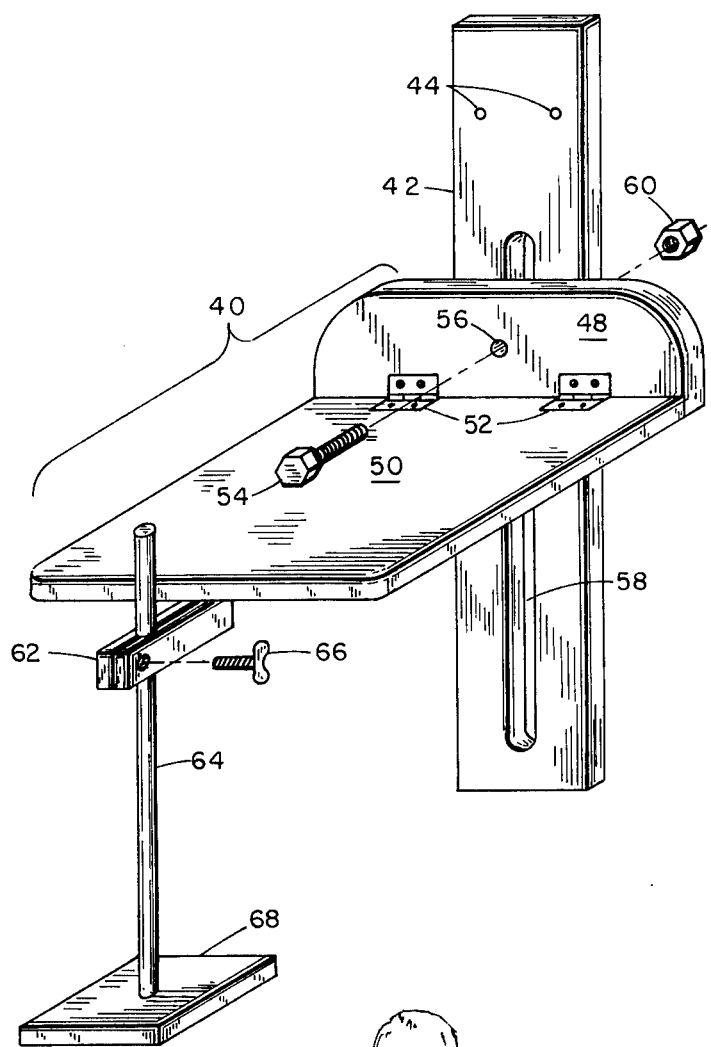
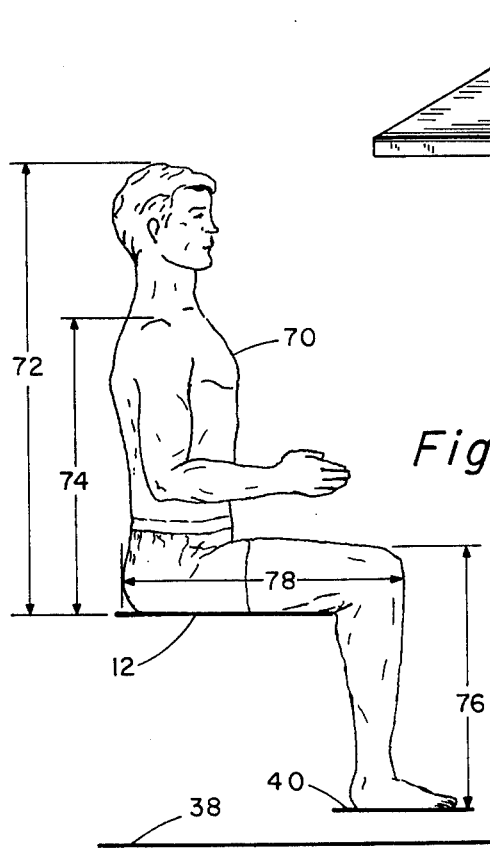
Fig. 3
Fig. 4
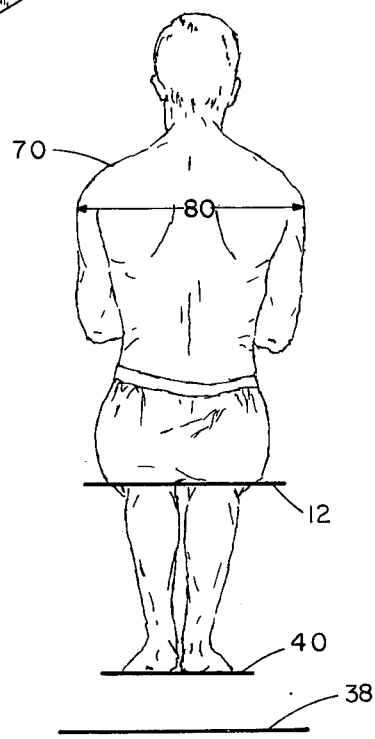

PORTABLE SEATING APPARATUS

BACKGROUND OF THE INVENTION

The present invention pertains to portable seating apparatus, and particularly to such apparatus which may usefully be employed for acquiring anthropometric information.

Reliable anthropometric data is increasingly important in designing equipment adaptable to users having a wide range of anatomical characteristics. For certain applications, it may be desirable or necessary to obtain required anthropometric data by measuring selected body dimensions of groups of subjects at geographically separated locations, who are representative of a particular class or population. For example, it may be necessary to acquire anthropometric information in this manner to assist in the design of protective equipment which will be adaptable to any member of any law enforcement agency.

To acquire anthropometric data based on uniform measuring instruments and procedures for the above or other purposes, a measuring team may successively move to different locations and employ anthropometric devices which are generally known to measure selected body dimensions of each member of a group of subjects. Measurement of certain significant dimensions, such as sitting height and buttock-knee length, requires that a subject be in a seated position, and uniformity of measurement is enhanced if an adjustable foot support is available to insure that the subject's thighs will be parallel to the floor and his calves perpendicular, regardless of the subject's leg length. However, a suitable foot support, or even a suitable seating bench, may not readily be available at each site of measurement, whereas structures for adequately positioning subjects may be too heavy or bulky for practical transport to every site. In addition, anthropometric measuring devices such as scales or various kinds of calipers may be quite delicate and may become damaged or misplaced in moving between measuring sites.

SUMMARY OF THE INVENTION

The present invention discloses an apparatus which in a closed position may be readily transportable, and in an open position may be employed to erectly seat and support the feet of a subject of selected anthropometric measurements. The apparatus may thereby be used to provide a standard anthopometric bench for measurements to be made at geographically separated measuring sites, although it is not intended to limit the invention to applications in the field of anthropometry. The apparatus generally comprises a containing means, which alternately may be used for a carrying case or for the upper portion of a seating bench, a seating support means for supporting the upper portion of the bench and feet supporting means for supporting or otherwise positioning the feet of a subject seated on the bench, regardless of his or her leg length. The dimensions of the respective elements of the apparatus are selected to enable the seating and foot support means as well as various anthropometric materials and measuring devices, such as steel tapes, weight scales, anthropometers, and several kinds of calipers, to be contained within the containing means when the invention is in a closed position. The containing means may be carried by one or two persons and may be taken aboard aircraft or other conveyances as a conventional piece of luggage.

OBJECTS OF THE INVENTION

An object of the invention is to provide a new and improved portable seating bench provided with an adjustable foot support.

Another object of the invention is to provide a new and improved seating bench which may be employed to standardize anthropometric measurements of seated subjects at different locations.

Another object is to provide a new and improved means for suitably positioning subjects of anthropometric measurements.

Other objects and may of the attendant advantages of this invention will be readily appreciated as the same become better understood by reference to the following detailed description when considered in connection with the accompanying drawings.

BRIEF DESCRIPTION OF THE DRAWINGS

FIG. 3 is an assembled view showing a foot support structure for the embodiment of FIG. 2.

FIG. 4 is a diagrammatic view of a subject showing a manner in which the embodiment of FIG. 2 may usefully be employed to acquire anthropometric data.

DESCRIPTION OF THE PREFERRED EMBODIMENTS

Figure 1:
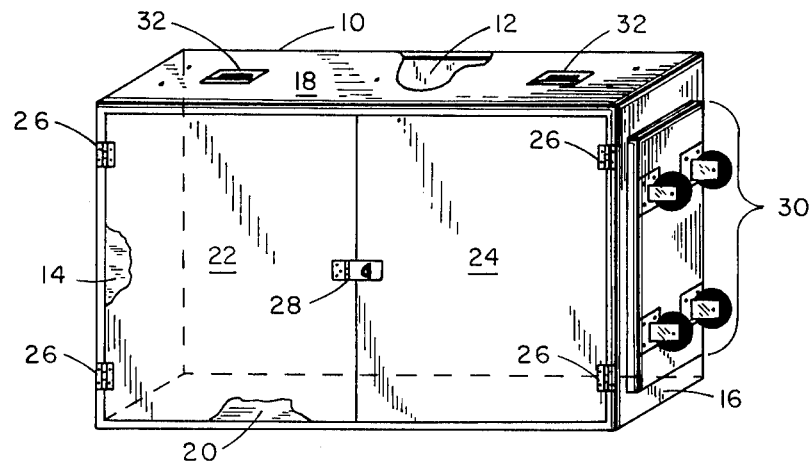
FIG. 1 is an assembled view showing a containing means for an embodiment of the invention in a folded stored condition.

Referring to FIG. 1, reference numeral 10 refers to a case or containing means comprising seating panel 12, which may usefully be a flat rectangular member, side panels 14, 16, 18, and 20, each having an edge perpendicularly joined to an edge of seating panel 12, and movable panels 22 and 24 pivotally attached to side panels 14 and 16, respectively, by means of hinges 26 or the like. Complementing parts of hasp 28 or other fastening means may be positioned on movable panels 22 and 24 to securely fasten containing means 10, and the dimensions of containing means 10 are sufficient to enable storage or transport therein of other structure, equipment, and material required to acquire anthropometric data from seated subjects. Casters 30 and carrying handles 32 may be to attached one or more of the side panels of containing means 10 for increased mobility.

Figure 2:
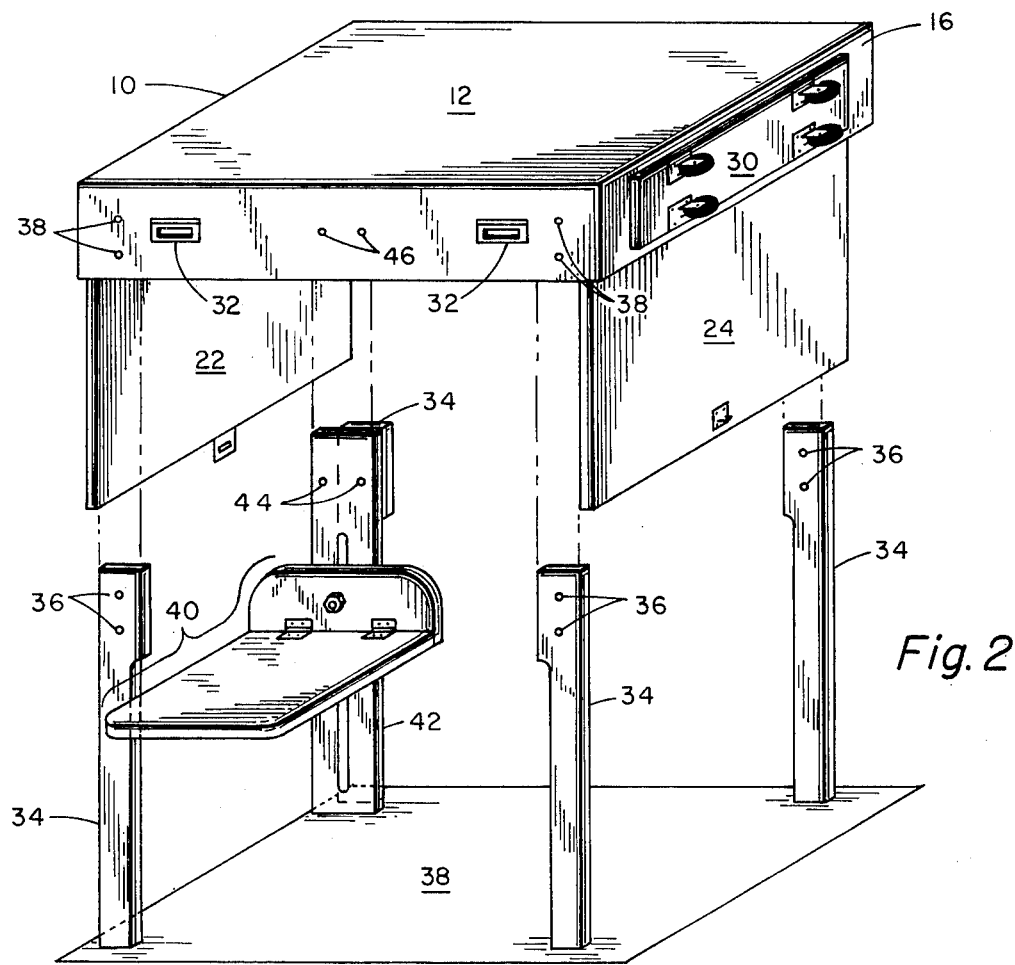
FIG. 2 is an exploded assembled view showing an embodiment of the invention in an open position.

Referring to FIG. 2, there are shown four leg members 34 which may be removably attached to containing means 10 in any suitable manner, for example, by matching each set of holes 36 through a leg member 34 with a corresponding set of holes 37 through a side panel of containing means 10, inserting bolts therethrough, and securing the bolts with wing nuts. Alternatively, leg members 34 may be pivotally attached to containing means 10.

Leg members 34 comprise a seating support means or structure for holding seating panel 12 in fixed parallel relation with horizontal surface 38, which may be a floor or other suitably hard horizontal surface, movable panels 22 and 24 freely hanging downward. The dimensions of the rectangular surface of seating panel 12 and of leg members 34 are selected to enable any subject of anthropometric measurement or other person to be seated upon seating panel 12 without the subject's feet touching surface 38.

Foot panel 40, slidably attached to foot panel support member 42 provides a flat surface which may be of any suitable shape and dimensions and may be vertically adjusted to rest or support the feet of any person seated upon seating panel 12, whereby the thighs of the seated person are parallel to surface 38 and his calves perpendicular, foot panel 40 and foot panel support member 42 comprising foot support means or structure. Foot panel support member 42 is removably attached to containing means 10 in any suitable manner, for example, by matching a set of holes 44 through member 42 with a corresponding set of holes 46 through a side panel of containing means 10, inserting bolts therethrough, and securing the bolt with wing nuts.

Referring to FIG. 3, there is shown foot panel 40 comprising vertical member 48 and horizontal member 50 pivotally attached by hinges 52 or the like whereby vertical member 48 may be folded over horizontal member 50 for storage or transportation in containing means 10. Foot panel 40 may be slidably attached to foot panel support member 42 in any suitable manner, for example, by inserting a bolt 54 through both a hole 56 in vertical member 48 and a longitudinal slot 58 in foot panel support member 42 and securing bolt 54 with a wing nut 60.

Additional foot support means or structure may be provided by resting foot panel 40 on clamping means 62, or alternatively attaching foot panel 40 thereto, clamping means 62 being movably positioned along stanchion longitudinal member 64 by tightening screw 66. Stanchion longitudinal member 64 may be removably attached in any suitable manner to stanchion base 68, which may be placed on surface 38, whereby the foot support structure may be capable of supporting the entire weight of a subject or other person.

Referring to FIG. 4, there is shown a subject of anthropometric measurement 70 erectly seated on seating panel 12, the subject's feet being supported by suitable adjustment of foot panel 40 above horizontal surface 38. While so positioned, the subject's sitting height 72, sitting shoulder height 74 and sitting knee height 76, may be measured by means of an anthropometer or other suitable linear measuring instrument, and buttock-knee length 78 and should breatdh, 80 may be measured by means of a beam caliper. Other anthropometric measurements may also be made using various devices while subject 70 is so positioned.

Obviously many modifications and variations of the present invention are possible in the light of the above teachings. It is therefore to be understood that within the scope of the appended claims the invention may be practiced otherwise than as specifically described.

What is claimed:

1. A portable anthropometric measurement apparatus having a closed portable position convertible into an open operative measurement position which comprises:
   a. rectangular enclosure for storing and transporting other elements of said apparatus when said apparatus is in the closed position;
   b. one side of said enclosure being flat to provide a horizontal seat for supporting a subject to be seated for said anthropometric measurements when said apparatus is in an open position;
   c. a plurality of detachable legs attachable to said enclosure for supporting said horizontal seat in an elevated position and capable of being stowed within the enclosure;
   d. a foot support means having a horizontal flat member detachably mounted to said enclosure and vertically adjustable for measuring the knee height of the subjects above the foot supporting member; and
   e. transporting means mounted on the enclosure.

2. The apparatus of claim 1 wherein said horizontal flat member of the foot support means is hinged for stowage.

3. The apparatus of claim 1 wherein said foot support means is hinged to a vertical support member, and means are provided for vertically adjusting the position of the flat foot member with respect to the vertical support member for measuring various knee heights.

4. The apparatus of claim 1 wherein said enclosure is provided with a set of hinged closure doors at a side opposite the seat side.

5. The apparatus of claim 4 wherein said enclosure has a plurality of perpendicular end walls extending from the seat to which said doors are hinged.

6. The apparatus of claim 5 wherein a set of casters are secured to one of said end walls.

7. The apparatus of claim 5 wherein a carrying handle is secured to one of said end walls.

8. The apparatus of claim 1 wherein the dimension of the seat width will support the buttocks and the upper leg of the subjects being measured.

9. The apparatus of claim 3 wherein:
   a. said enclosure has a flat seat portion on one side and a plurality of perpendicularly extending end walls;
   b. a set of hinged doors secured to said side walls on the side of the enclosure opposite to said seat to close the enclosure; and
   c. means on a side wall for transporting the closed enclosure.

* * * * *